United States Patent [19]

Saito

[11] Patent Number: 4,974,590

[45] Date of Patent: Dec. 4, 1990

[54] ULTRASONIC PROBE FOR USE IN ULTRASONIC ENDOSCOPE

[75] Inventor: Yoshitake Saito, Kunitachi, Japan

[73] Assignee: Olympus Optical Co., Ltd., Tokyo, Japan

[21] Appl. No.: 350,458

[22] Filed: May 11, 1989

[30] Foreign Application Priority Data

May 18, 1988 [JP] Japan .................. 63-119315

[51] Int. Cl.⁵ .............................................. A61B 8/12
[52] U.S. Cl. .............................................. 128/662.06
[58] Field of Search ................ 128/662.05, 662.06, 128/660.09, 660.10, 4, 6

[56] References Cited

U.S. PATENT DOCUMENTS 4,819,652  4/1989  Micco .................... 128/661.09
4,834,102  5/1989  Schwarzchild et al. ....... 128/662.06

FOREIGN PATENT DOCUMENTS

3024457  4/1981  Fed. Rep. of Germany .
3537904  4/1986  Fed. Rep. of Germany .
3615390  11/1986  Fed. Rep. of Germany .
3716964  11/1987  Fed. Rep. of Germany .

Primary Examiner—Francis Jaworski
Attorney, Agent, or Firm—Stevens, Davis, Miller & Mosher

[57] ABSTRACT

An ultrasonic probe for use in the ultrasonic endoscope including a damping layer arranged on a rear surface of an ultrasonic vibrating element for absorbing an undesired ultrasonic wave emitted from the rear surface of the vibrating element, an insulating layer and a conductive housing. A matching coil for improving the efficiency of the vibration of the ultrasonic vibrating element is formed as an air-core type and is embedded within the damping layer or the insulating layer such that the undesired ultrasonic wave is passed through a hollow central space of the air-core type matching coil and is effectively absorbed by the damping layer, so that the damping function of the damping layer is not affected by the matching coil.

10 Claims, 6 Drawing Sheets

FIG.8

ULTRASONIC PROBE FOR USE IN ULTRASONIC ENDOSCOPE

BACKGROUND OF THE INVENTION

Field of the Invention and Related Art Statement

The present invention relates to an ultrasonic probe for use in an ultrasonic endoscope.

Similar to ultrasonic probes used in various fields of diagnoses, the ultrasonic probe for use in the ultrasonic endoscope can inspect the construction of a body under inspection by applying an electric signal to electrodes applied on opposite surfaces of a piezo-electric element to emit an ultrasonic wave toward the body, receiving an ultrasonic wave reflected by the body, converting the received wave into an electric echo signal, and processing the electric echo signal to display an ultrasonic image of the body. The ultrasonic probe for use in the endoscope has to be constructed extremely small in size, because the ultrasonic probe is arranged in a distal end of a very thin insertion section of the endoscope which is insertable into a cavity of the body.

Figure 1:
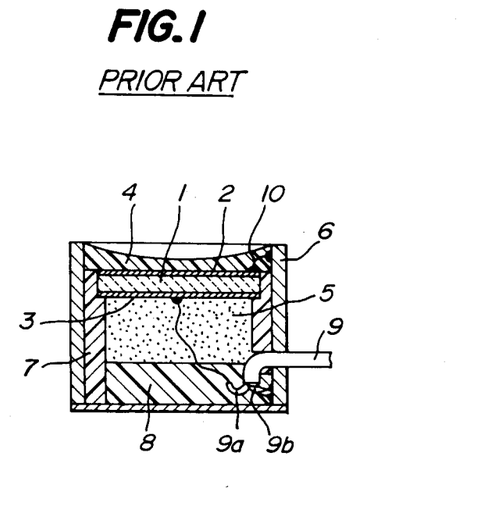
FIG. 1 is a cross sectional view showing the construction of the known ultrasonic probe.

FIG. 1 is a cross sectional view showing the construction of a known ultrasonic probe for use in an ultrasonic endoscope. The ultrasonic probe comprises a piezo-electric element 1 made of piezo-electric material such as PZT. On opposite surfaces of the piezo-electric element 1 are applied a front surface electrode 2 and a rear surface electrode 3, respectively. By applying an electric signal, particularly a pulse signal across these electrodes 2 and 3, the piezo-electric element 1 is vibrated to emit an ultrasonic wave. On the front surface electrode 2 there is provided a lens layer 4 for converging the ultrasonic wave emitted by the piezo-electric element 1.

On the rear surface electrode 3 there is provided a damping layer 5 for absorbing an undesired ultrasonic wave emitted from the rear surface electrode 3. The damping layer 5 may be made of a synthetic resin such as epoxy resin having conductive material particles such as tungsten powder embedded therein, so that the damping layer is generally electrically conductive. The piezo-electric element 1, lens layer 4 and damping layer 5 are mounted in a housing 6 made of, for instance metal by means of an insulating layer 7 in the form of a sleeve. A core wire 9a of a signal cable 9 for supplying the electric signal to the piezo-electric element 1 is connected to the rear surface electrode 3 and a shielding conductor 9b of the cable 9 is connected to the front surface electrode 2 by soldering the shielding conductor to the housing 6 and by connecting the housing to the front surface electrode 2 by means of a conductive wire 10. Since the damping layer 5 has the electrical conductivity, it is required to prevent the short-circuiting between the front and rear surface electrodes 2 and 3 via the damping layer. To this end, on a rear surface of the damping layer 5 is provided an insulating layer 8.

Figure 2:
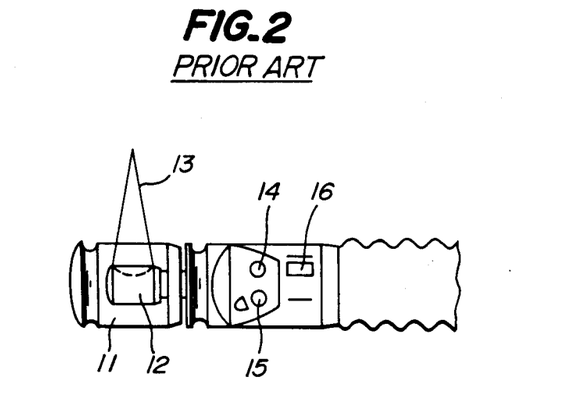
FIG. 2 is plan view illustrating an end portion of the ultrasonic endoscope having the known ultrasonic probe.
Figure 3:
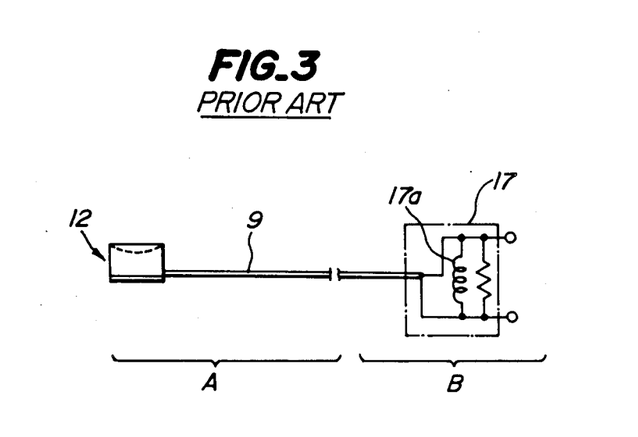
FIG. 3 is a schematic view depicting the manner of connecting the matching coil in the known ultrasonic probe.

FIGS. 2 and 3 illustrate the known ultrasonic endoscope having the known ultrasonic probe. FIG. 2 shows the construction of a distal end of the insertion section of the endoscope. Inside a cap 11 there is arranged an ultrasonic probe 12 which emits an ultrasonic wave 13. A reference numeral 14 denotes a light guide for illuminating the body under inspection, 15 represents an objective lens for forming an optical image of the body and 16 shows an opening of a forceps channel through which various kinds of forceps can be inserted. FIG. 3 is a schematic view illustrating a portion of the endoscope, in which a portion A represents an insertion section which is insertable into the cavity of the body and a portion B denotes the remaining portion, i.e. a portion outside the body.

In the ultrasonic probe shown in FIG. 1, since the lens layer 4 and damping layer 5 are directly applied on the piezo-electric element 1, the electrostatic capacitance of the element 1 is equivalently increased and thus the vibrating efficiency of the element is liable to be decreased. It has been known to increase the vibrating efficiency of the element 1 by providing a matching circuit 17 including a matching coil 17a as illustrated in FIG. 3. In the ultrasonic endoscope, since it is necessary to make the ultrasonic probe as small as possible, the matching coil 17a has to be provided in the portion B as shown in FIG. 3.

On the other hand in order to obtain the ultrasonic image having the high resolution, it is required to increase the frequency of the ultrasonic wave. In this case, the matching coil 17a is arranged at the proximal end of the cable 9, the electrostatic capacitance and ohmic resistance of the relatively long cable 9 could be no more ignored, so that the resonance point of the ultrasonic vibrating element including the piezo-electric element 1 and surface electrodes 2 and 3 might be shifted from a designed resonance point and the sufficient matching could not be attained. In this manner, the ultrasonic vibrating element could not be vibrated at a desired high frequency. It should be noted that the above mentioned capacitance and ohmic resistance of the signal cable do not affect seriously the function of the element 1 when the vibrating frequency is rather low such as 1 to 7.5 MHz.

SUMMARY OF THE INVENTION

The present invention has for its object to provide a novel and useful ultrasonic probe which can remove the above mentioned drawback and can increase the vibrating frequency of the piezo-electric ultrasonic vibrating element without increasing the size of the probe and can provide the ultrasonic image having the high resolution.

According to the invention, in order to attain the above object an ultrasonic probe for use in an ultrasonic endoscope comprises
- an ultrasonic vibrating element for emitting an ultrasonic wave;
- a damping layer arranged on a rear surface of the ultrasonic vibrating element for absorbing an ultrasonic wave emitted from the rear surface of the ultrasonic vibrating element;
- an insulating layer arranged to surround the damping layer;
- an electrically conductive housing for accommodating the ultrasonic vibrating element, damping layer and insulating layer; and
- an air-core type matching coil arranged within the housing.

In the ultrasonic probe according to the present invention, since the air-core type matching coil is arranged in the housing in which the piezo-electric element is also provided, the capacitance and resistance of the cable do not have any influence upon the resonance, so that the piezo-electric element can vibrate at a desired high frequency with a high efficiency.

DESCRIPTION OF THE PREFERRED EMBODIMENTS

Figure 4:
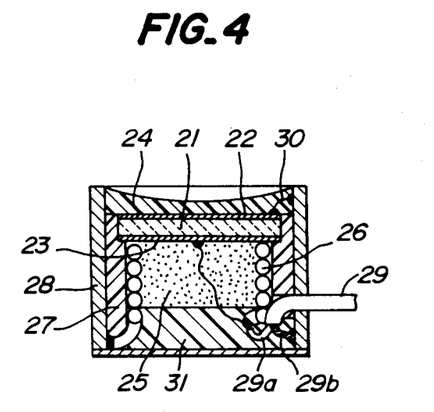
FIG. 4 is a cross sectional view showing an embodiment of the ultrasonic probe according to the invention.

FIG. 4 is a cross sectional view showing an embodiment of the ultrasonic probe according to the invention. The ultrasonic probe comprises a piezo-electric element 21 having front and rear surface electrodes 22 and 23 applied on opposite surfaces of the piezo-electric element. On the front surface electrode 22 there is arranged a lens layer 24 for converging an ultrasonic wave emitted in the side of the front surface of the piezo-electric element 21. On the rear surface electrode 23 there is arranged a damping layer 25 for absorbing an undesired ultrasonic wave emitted in the side of the rear surface electrode 23. In the present embodiment, a hollow matching coil 26 of air-core type is embedded in the damping layer 25 such that an axis of the coil is aligned with the direction of the ultrasonic wave emitted from the front surface electrode 22. The damping layer 25 is arranged in a housing made of metal by means of an insulating layer 27. A core conductor 29a of a signal cable 29 is directly soldered to the rear surface electrode 23 and a shielding conductor 29b of the cable 29 is soldered to the housing 28 and the housing is connected to the front surface electrode 22 via a conductive wire 30. One end of the air-core type matching coil 26 is connected to the housing 28 and the other end thereof is connected to the core conductor 29a of the signal cable 29. An insulating layer 31 is further provided on the rear surface of the conductive damping layer 25 for preventing the short circuit between the front and rear surface electrodes 22 and 23. Since the damping layer 25 has the electrical conductivity, the matching coil 26 is made by a conductive wire having an insulating coating applied thereon.

In the present embodiment, the matching coil 26 is embedded in the damping layer 25, so that the whole size of the ultrasonic probe is not increased at all. Further, the matching coil 26 is of the air-core type, so that the function of the damping layer 25 is not affected, because the undesired ultrasonic wave emitted from the rear surface electrode 23 can pass through the air-core of the matching coil freely. It should be noted that the matching coil 26 is arranged in the vicinity of the piezo-electric element 21, and thus the matching can be attained without being affected by the signal cable 29 so that the piezo-electric element 21 can vibrate at a desired high frequency with a high efficiency.

Figure 5:
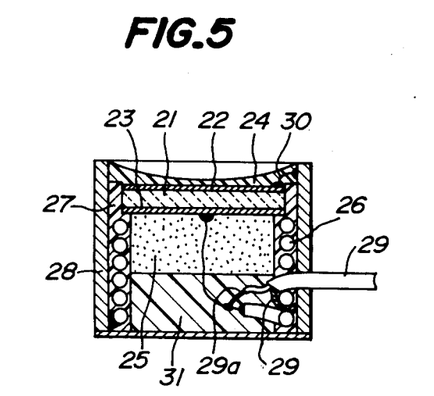
FIG. 5 is a cross sectional view depicting another embodiment of the ultrasonic probe according to the invention.

FIG. 5 is a cross sectional view showing a second embodiment of the ultrasonic probe according to the invention. In the present embodiment, the air-core matching coil 26 is embedded in the insulating layer 27 provided between the damping layer 25 and the housing 28. The remaining construction of the ultrasonic probe is same as the previous embodiment. It should be noted that in the present embodiment, since the matching coil 26 is provided in the insulating layer 27, it is no more necessary to construct the coil by the insulated conductive wire. Also in the second embodiment, the desired matching can be obtained without increasing the size of the ultrasonic probe and the piezo-electric element can vibrate at a high frequency. It is matter of course that the matching coil 26 does not affect the function of the damping layer 25.

Figure 6:
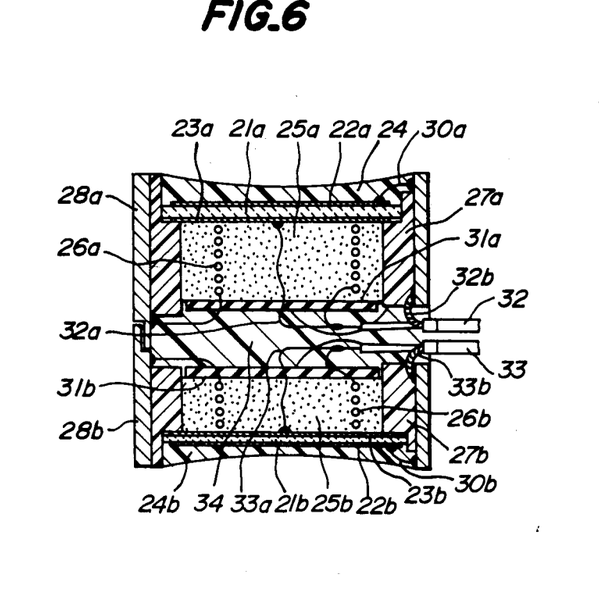
FIG. 6 is a cross sectional view illustrating still another embodiment of the ultrasonic probe according to the invention.

FIG. 6 is a cross sectional view illustrating a third embodiment of the ultrasonic probe according to the invention. In the present embodiment, two ultrasonic vibrating elements having different frequencies are arranged in a back to back manner. The two ultrasonic vibrating elements vibrate at 7.5 MHz and 12 MHz, respectively and the construction of these elements is same as that of the previous embodiments, so that portions corresponding to those of the previous embodiments are denoted by the same reference numerals with suffixes of a and b, respectively. In the present embodiment, air-core type matching coils 26a and 26b are arranged in damping layers 25a and 25b, respectively. Core conductors 32a and 33a of signal cables 32 and 33 are connected to rear surface electrodes 23a and 23b, respectively as well as to matching coils 26a and 26b, respectively. Shielding conductors 32b and 33b of the cables 32 and 33 are connected to the front surface electrode 22a and 22b, respectively by means of metal housing 28a, 28b and conductive wires 30a, 30b, respectively. It should be noted that the outer insulating coatings of the signal cables 32 and 33 have different colors so that they can be easily delineated from each other. The two housings 28a and 28b are coupled with each other with an adhesive agent and an insulating layer 34 is provided between these housings to form an integral body.

Figure 7:
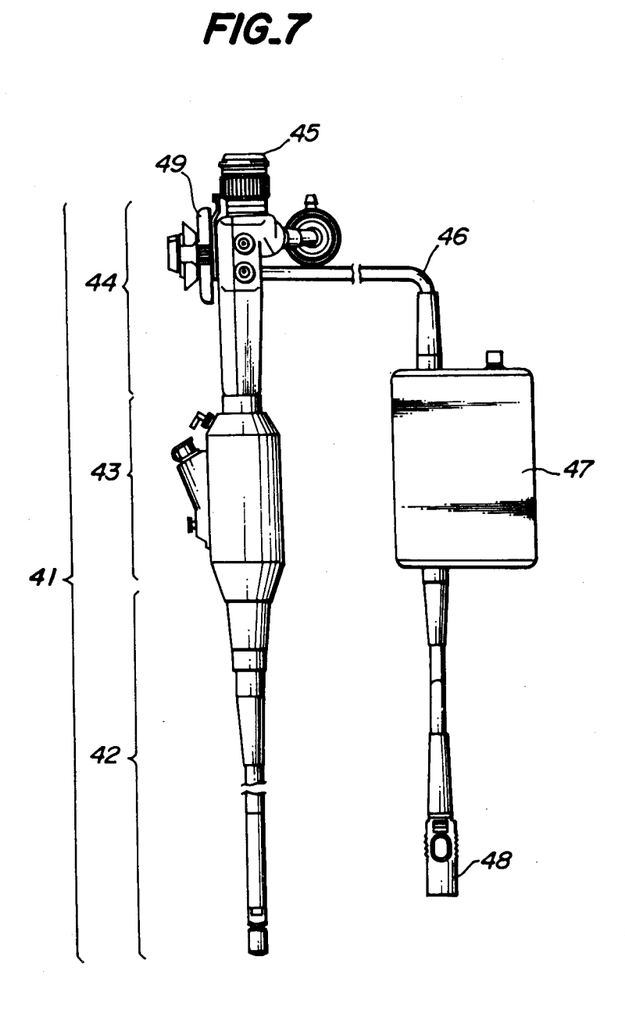
FIG. 7 is a front view representing the whole construction of the ultrasonic endoscope having the probe shown in FIG. 6.
Figure 8:
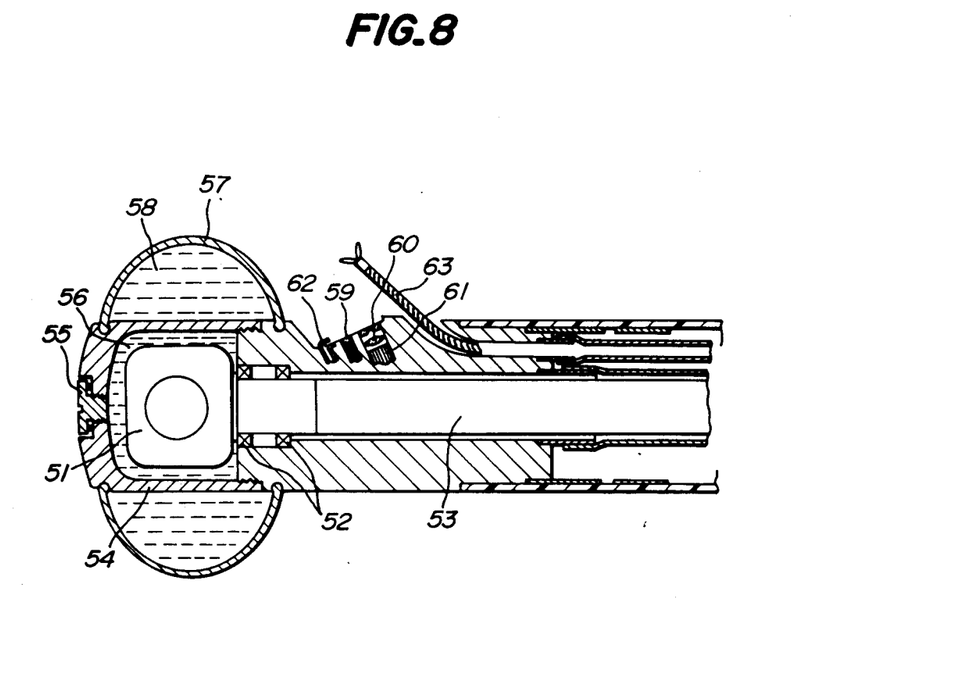
FIG. 8 is a cross sectional view illustrating the construction of the distal end of the ultrasonic endoscope shown in FIG. 7.

FIG. 7 is a front view showing the whole construction of the ultrasonic endoscope having the ultrasonic probe shown in FIG. 6, and FIG. 8 is a cross sectional view illustrating the construction of the distal end of the endoscope. An ultrasonic endoscope 41 comprises a flexible insertion section 42 which is insertable into a cavity of a body under inspection, an ultrasonic operation section 43 connected to a proximal end of the insertion section 42, an endoscope operation section 44 coupled with the ultrasonic operation section 43, an eyepiece section 45 provided on the endoscope operation section 44, and a signal cable 46 for connecting the endoscope 41 to a driving and inspecting apparatus (not shown). In the cable 46 there is connected an intermediate box 47 including electric circuits and switches, and a connector 48 is provided at an end of the signal cable 46. In the ultrasonic operation section 43 there are arranged a motor for rotating the ultrasonic probe provided in the distal end of the insertion section 42 to effect the ultrasonic scanning, an opening of a forceps channel, and various kinds of operating members for controlling the supply of the air and water. On the endoscope operation section 44 there is arranged a handle 49 for bending the distal end of the insertion section 42.

As illustrated in FIG. 8, in the distal end of the insertion section 42 the ultrasonic probe 51 shown in FIG. 6 is arranged rotatably by means of bearings 52, and a flexible shaft 53 is connected to the ultrasonic probe 51, the shaft being coupled with the motor provided in the ultrasonic operation section 43. The ultrasonic probe 51 is surrounded by a cover 54 made of synthetic resin which can pass the ultrasonic wave. Within the cover 54 an ultrasonic wave propagating liquid 56 is injected from a hole which is plugged by a screw 55. Further a balloon 57 is arranged detachably on the distal end of the insertion section 42. During the inspection, the balloon 57 is filled with an ultrasonic wave propagating liquid 58. Moreover, in the insertion section 42 there are arranged light guide 59, objective lens 60, image guide 61 and water supply nozzle 62 for cleaning the optical system for inspecting the optical image of the body. There is further arranged within the insertion section 42 a forceps channel through which a forceps 63 can be inserted into the body. The construction of the endoscope except for the ultrasonic probe 51 is same as the known endoscope, so that further detailed explanation is dispensed with.

The present invention is not limited to the embodiments explained above, but many alternations and modifications may be conceived by those skilled in the art within the scope of the invention. For instance, the air-core type matching coil may be constructed as a double coil having inner and outer coil halves which are arranged coaxially. In this case, the dimension of the coil measured in the axial direction thereof can be reduced, so that the size of the ultrasonic probe can be also decreased in the axial direction. Further, the matching coil may be arranged at different positions within the housing than those shown in the drawings. For example, the matching coil may be provided between the damping layer 25 and the insulating layer 27. In case of arranging the matching coil within the electrically conductive damping layer, it is necessary to construct the coil from the conductive wire having the insulating coating, but if the damping layer is electrically insulating, it is no more necessary to form the coil by the insulating conductive wire.

What is claimed is:

1. An ultrasonic probe for use in an ultrasonic endoscope, said ultrasonic probe comprising:
    an ultrasonic vibrating element for emitting an ultrasonic wave;
    a damping layer arranged on a rear surface of the ultrasonic vibrating element for absorbing an ultrasonic wave emitted from the rear surface of the ultrasonic vibrating element;
    an insulating layer arranged to surround the damping layer;
    an electrically conductive housing means in which the ultrasonic vibrating element, damping layer and insulating layer are housed; and
    an air-core type matching coil embedded in the damping layer.

2. An ultrasonic probe according to claim 1, wherein said air-core type matching coil is arranged such that an axial direction of the matching coil is disposed in parallel with an ultrasonic wave propagating direction in which ultrasonic waves are emitted from the ultrasonic vibrating element.

3. An ultrasonic probe according to claim 2, wherein said air-core matching coil is arranged such that the axial direction of the matching coil is aligned with the ultrasonic wave propagating direction.

4. An ultrasonic probe according to claim 1, further comprising another said ultrasonic vibrating element and another said insulating layer arranged between the two ultrasonic vibrating elements.

5. An ultrasonic probe according to claim 1, wherein said ultrasonic vibrating element includes a piezo-electric element, a front surface electrode applied on a front surface of the electric element, and a rear surface electrode applied on a rear surface of the piezo-electric element, a core conductor comprising a signal cable for supplying an electric signal to the ultrasonic vibrating element is connected to the rear surface electrode and a shielding conductor of the signal cable is connected to the housing which is connected to the front surface electrode by means of a conductive wire, and one end of the matching coil is connected to the rear surface electrode and the other end of the matching coil is connected to the housing.

6. An ultrasonic probe for use in an ultrasonic endoscope, said ultrasonic probe comprising:
    an ultrasonic vibrating element for emitting an ultrasonic wave;
    a damping layer arranged on a rear surface of the ultrasonic vibrating element for absorbing an ultrasonic wave emitted from the rear surface of the ultrasonic vibrating element;
    an insulating layer arranged to surround the damping layer;
    an electrically conductive housing in which said ultrasonic vibrating element, damping layer and insulating layer are housed; and
    an air-core type matching coil embedded in the insulating layer.

7. An ultrasonic probe according to claim 6, wherein said air-core type matching coil is arranged such that an axial direction of the matching coil is disposed in parallel with an ultrasonic wave propagating direction in which ultrasonic waves are emitted from the ultrasonic vibrating element.

8. An ultrasonic probe according to claim 7, wherein said air-core type matching coil is arranged such that said axial direction of the matching coil is aligned with said ultrasonic wave propagating direction.

9. An ultrasonic probe for use in an ultrasonic endoscope, said ultrasonic probe comprising:
    an ultrasonic vibrating means for emitting ultrasonic waves, said ultrasonic vibrating means comprising a first vibrating element and a second vibrating element disposed in back-to-back relationship;
    a first damping layer arranged on a rear surface of said first vibrating element for absorbing an ultrasonic wave emitted from the rear surface of the first vibrating element and a second damping layer arranged on a rear surface of said second vibrating element for absorbing an ultrasonic wave emitted from the rear surface of the second vibrating element;
    an insulating layer means arranged to surround the first damping layer and the second damping layer;
    an electrically conductive housing means in which said first vibrating element, said second vibrating element, said first damping layer, said second damping layer and said insulating layer means are housed; and a first air-core type matching coil embedded in said first damping layer and a second air-core type matching coil embedded in said second damping layer.

10. An ultrasonic probe for use in an ultrasonic endoscope, said ultrasonic probe comprising:

a first ultrasonic vibrating element for emitting an ultrasonic wave and a second ultrasonic vibrating element for emitting an ultrasonic wave;

a first damping layer arranged on a rear surface of the first ultrasonic vibrating element for absorbing an ultrasonic wave emitted from the rear surface of the first ultrasonic vibrating element and a second damping layer arranged on a rear surface of the second ultrasonic vibrating element for absorbing an ultrasonic wave emitted from the rear surface of the second ultrasonic vibrating element;

a first insulating layer arranged to surround the first damping layer, a second insulating layer arranged to surround the second damping layer, and another insulating layer arranged between the first ultrasonic vibrating element and the second ultrasonic vibrating element; and a first housing in which said first vibrating element, said first damping layer and said first insulating layer are housed and a second housing in which said second vibrating element, said second damping layer and said second insulating layer are housed, said first housing and said second housing being coupled with each other to form an integral body.

* * * * *